(12) United States Patent
Lovmar et al.

(10) Patent No.: US 10,920,092 B2
(45) Date of Patent: Feb. 16, 2021

(54) ANTIBACTERIAL COATING OR SURFACE COMPRISING VERTICAL, STANDING ANGSTROM SCALE FLAKES

(71) Applicant: DENTSPLY IH AB, Mölndal (SE)

(72) Inventors: Martin Lovmar, Mölndal (SE); Santosh Pandit, Gothenburg (SE); Venkata R. S. S. Mokkapati, Gothenburg (SE); Jie Sun, Västra Frölunda (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

(21) Appl. No.: 15/971,482

(22) Filed: May 4, 2018

(65) Prior Publication Data

US 2018/0320002 A1 Nov. 8, 2018

(30) Foreign Application Priority Data

May 5, 2017 (EP) .................................... 17169738

(51) Int. Cl.
| | |
|---|---|
| *C09D 5/16* | (2006.01) |
| *A61L 29/10* | (2006.01) |
| *A61L 31/02* | (2006.01) |
| *A61L 27/30* | (2006.01) |
| *A61L 31/08* | (2006.01) |
| *A61L 27/08* | (2006.01) |
| *A61L 29/02* | (2006.01) |
| *C01B 32/205* | (2017.01) |
| *C01B 32/182* | (2017.01) |
| *C09D 7/61* | (2018.01) |
| *A61M 25/00* | (2006.01) |
| *B82Y 30/00* | (2011.01) |
| *C23C 16/26* | (2006.01) |

(52) U.S. Cl.
CPC ............ *C09D 5/1618* (2013.01); *A61L 27/08* (2013.01); *A61L 27/303* (2013.01); *A61L 29/02* (2013.01); *A61L 29/103* (2013.01); *A61L 31/024* (2013.01); *A61L 31/084* (2013.01); *A61M 25/0043* (2013.01); *C01B 32/182* (2017.08); *C01B 32/205* (2017.08); *C09D 7/61* (2018.01); *A61L 2300/404* (2013.01); *A61L 2400/12* (2013.01); *A61L 2400/18* (2013.01); *A61M 25/0017* (2013.01); *A61M 2025/0056* (2013.01); *B82Y 30/00* (2013.01); *C01B 2204/32* (2013.01); *C23C 16/26* (2013.01)

(58) Field of Classification Search
CPC ....... C09D 5/1618; C09D 7/61; A61L 29/103; A61L 31/024; A61L 27/303; A61L 31/084; A61L 27/08; A61L 29/02; A61L 2400/12; A61L 2400/18; A61L 2300/404; C01B 32/205; C01B 32/182; C01B 2204/32; A61M 25/0017; A61M 2025/0056; C23C 16/26

See application file for complete search history.

(56) References Cited

U.S. PATENT DOCUMENTS

| | | | |
|---|---|---|---|
| 6,364,903 B2 * | 4/2002 | Tseng | A61F 2/07 427/2.24 |
| 9,919,093 B2 | 3/2018 | Andreen et al. | |
| 2013/0331781 A1 | 12/2013 | Andreen | |
| 2014/0005602 A1 | 1/2014 | Andreen et al. | |
| 2014/0155864 A1 | 6/2014 | Andreen | |
| 2016/0193403 A1 | 7/2016 | Andersson | |

FOREIGN PATENT DOCUMENTS

| | | |
|---|---|---|
| WO | 2013109891 | 7/2013 |
| WO | 2015113056 | 7/2015 |
| WO | 2017065625 | 4/2017 |

OTHER PUBLICATIONS

Ramakrishna Podila, et al, Graphene Coatings for Biomedical Implants, 73 J Vis. Exp. E50276 (Year: 2013).*
Fabricio Borghi, Fabrication and Biological Applications of Graphene-Based Nanostructures, Doctoral Thesis, University of Sydney (available at http://hdl.handle.net/2123/15657) (Year: 2016).*
Hu, W. et al., Graphene-based antibacterial paper, ACS Nano, 2010, 4317-4323, 4(7).
Liu, S. et al., Antibacterial activity of graphite, graphite oxide, graphene oxide, and reduced graphene oxide: Membrane and Oxidative Stress, ACS Nano, 2011, 6971-6980, 5(9).
Tu, Y. et al., Destructive extraction of phospholipids from *Escherichia coli* membranes by graphene nanosheets, Nat. Nanotechnology, 2013, 594-601, 8.
Liu, S. et al., Lateral dimension-dependent antibacterial activity of graphene oxide sheets, Langmuir, 2012, 12364-12372, 8.
Perreault, F. et al., Antimicrobial properties of graphene oxide nanosheets: why size matters, ACS Nano., 2015, 7226-7236, 9(7).
Ruiz, O. et al., Graphene oxide: a nonspecific enhancer of cellular growth, ACS Nano, 2015, 8100-8107, 5(10).
Ren, W. et al., Time-dependent effect of graphene on the structure, abundance, and function of the soil bacterial community, J. Hazard. Mater., 2015, 286-294, 297.
Wang, D. et al., Using graphene oxide to enhance the activity of anammox bacteria for nitrogen removal, Bioresour. Technol., 2013, 527-530, 131.

(Continued)

*Primary Examiner* — Sean M Basquill
(74) *Attorney, Agent, or Firm* — Perkins Coie LLP

(57) ABSTRACT

An antibacterial device is disclosed that includes a substrate and an antibacterial coating or antibacterial surface being provided on at least a part of the substrate's surface. The antibacterial coating or surface includes Angstrom scale flakes, where the Angstrom scale flakes are arranged in a standing position on the substrate surface and are attached to the substrate surface via edge sides thereof. The Angstrom scale flakes can, for example, be graphene flakes, or graphite flakes having a thickness of a few atom layers. It has been found that such standing flakes are efficient in killing prokaryotic cells but do not harm eukaryotic cells.

13 Claims, 14 Drawing Sheets

(56) References Cited

OTHER PUBLICATIONS

Li, X. et al., Large-area synthesis of high-quality and uniform graphene films on copper foils, Science, 2009, 1312-1314, 324.
Liu, L. et al., A mechanism for highly efficient electrochemical bubbling delamination of CVD-grown graphene from metal substrates, Adv. Mater. Interf., 2016, 1500492 (1-10), 3.
European Search Report for European Patent Application No. 17169738.6, dated Nov. 20, 2017 (9 pages).
Pandit, Santosh et al., "Toxicity of graphene towards the bacteria and mammalian cells", Graphene2017, Barcelona, Jan. 1, 2017.
Veltri, S. et al., "Synthesis and characterization of thin-transparent nanostructured films for surface protection", Superlattices and Microstructures, Academic Press, vol. 101, Nov. 15, 2016.

* cited by examiner

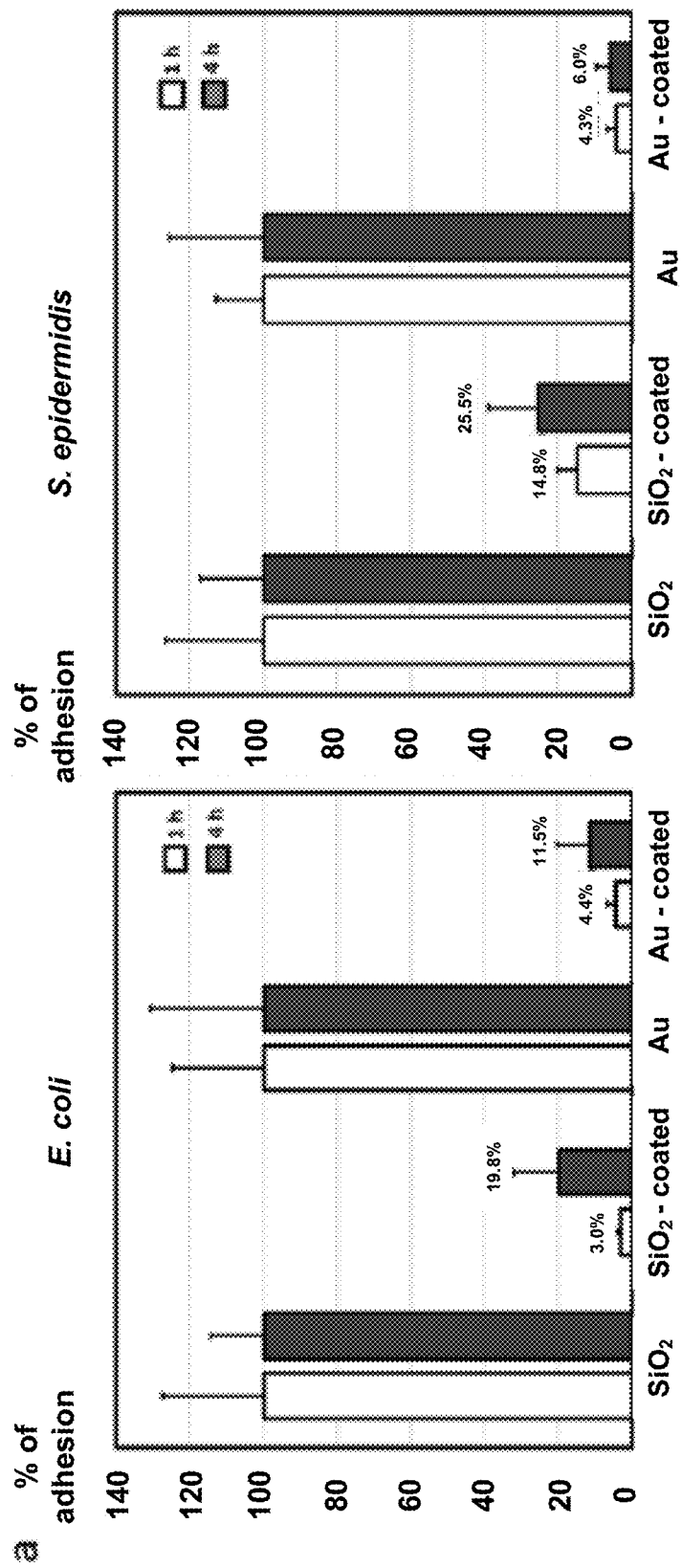

ANTIBACTERIAL COATING OR SURFACE COMPRISING VERTICAL, STANDING ANGSTROM SCALE FLAKES

CROSS-REFERENCE TO RELATED APPLICATIONS

This patent document claims the benefits and priority to European Patent Convention Application No. 17169738.6, filed on May 5, 2017, which is incorporated herein by reference in its entirety.

FIELD OF THE INVENTION

The present invention generally relates to an antibacterial device comprising a substrate and an antibacterial coating or antibacterial surface being provided on a surface or a part of a surface of the substrate. The invention also relates to a method for producing such an antibacterial device.

BACKGROUND

Bacterial infections are a big problem in the society, and there is a general need to reduce the number of bacteria in many situations, such as in tap water, in medical devices, etc.

One way of reducing bacteria is to clean and sterilize equipment, and to use products in a clean way, thereby avoiding contamination. However, despite adherence to sterile guidelines etc, the use of e.g. medical devices, and in particular introduction of medical devices into natural and artificial body openings, implies a risk of bacterial contamination. For example, insertion and maintenance of urinary catheters poses a problem in relation to catheter-associated infections. When medical devices such as a catheter is introduced into the human cavity, the normal human defense barrier may be penetrated, which can result in introduction of bacteria, fungi, vira, or tissue-like or multiple organized cells. Urinary tract infection (UTI), for instance, is a problem associated with the use of urinary catheters, and in particular for indwelling catheters, so-called Foley catheters, but also for catheters for intermittent use. It is estimated that almost one-quarter of hospitalized spinal cord-injured patients develop symptomatic UTI during their hospital course. Gram-negative bacilli account for almost 60-70 percent, enterococci for about 25 percent and *Candida* species for about 10 percent of cases of UTI. It is also well known that persons practicing intermittent urethral catheterization as a daily routine often have problems with symptomatic UTI.

Similar problems are present also in medical irrigation devices, such as devices for anal irrigation, vaginal irrigation, etc.

Thus, cleanliness, sterilization and the like is efficient to reduce the number of bacteria, but is often not sufficient.

Further, it is well known to use antibacterial agents/compounds to kill bacteria, such as antibiotics and the like, that either kills or inhibits growth of bacteria. The antibacterial agents may be administered directly to humans and animals, or be arranged in coatings on medical devices and other devices. However, the use of such antibacterial agents/compounds have several negative effects, such as the development of resistance of bacteria, and unwanted harmful side-effects. There is therefore a general need to limit the use of antibacterial agents/compounds, and in particular antibiotic drugs, to situations where it is of real necessity. Also, due to the increased emergence of bacteria resistance, the antibacterial effect for many known antibacterial agents is decreasing.

There is therefore a need for new and improved ways of killing bacteria and/or inhibiting growth of bacteria.

SUMMARY

It is a general object of the present invention to fulfil the above-discussed need and alleviate the above-discussed problems.

This object is fulfilled by an antibacterial device and a method in accordance with the appended claims.

According to a first aspect of the present invention, there is provided an antibacterial device comprising a substrate and an antibacterial coating or surface being provided on a surface or a part of a surface of the substrate, wherein said antibacterial coating or surface comprises Angstrom scale flakes, e.g. of graphene or graphite, the Angstrom scale flakes being arranged in a standing position on said surface, and attached to the surface via edge sides thereof.

In the present application, "Angstrom scale flake" refers to a flake or platelet, i.e. an even or uneven piece of material with one dimension, the thickness, substantially smaller than the other two dimensions (length and height), and where the thickness is of Angstrom scale or Angstrom dimension, i.e. between 1 and 100 Å (0.1-10 nm), and preferably between 1 and 50 Å (0.1-5 nm), and most preferably between 1 and 20 Å (0.1-2 nm). The flake is not necessarily flat but can assume both plate-like forms as well as various curved shapes.

The standing position of the flakes is preferably essentially perpendicular to the surface, but may also be slightly bent or tilted.

The flakes are preferably attached to the surface essentially individually, thereby forming free-standing, self-supported flakes with rigid integrity by themselves. Such a rigid structure preferably preserves the mechanical stability of the coating/surface, preventing that the flakes collapse and/or stack with each other in random directions, e.g. due to van der Waals interactions.

The flakes are preferably made of graphene or graphite. The graphene and graphite may be pure graphene/graphite, or doped materials. For example, the graphene may be doped with boron, nitrogen or the like, or modified in other, per se known ways. However, other 2D materials may also be used, such as graphyne, germanene, silicone, phosphorene, etc, may also be used. All the flakes are preferably of one material. However, combinations of flakes made of two or more materials are also feasible.

Graphene is a two-dimensional material having carbon atoms arranged in a honeycomb-like hexagonal lattice, and with a thickness of one atom. Due to its remarkable mechanical and electrical properties, graphene has been exploited in various applications, such as for producing enhanced electric contact surfaces. The interaction of graphene, and its derivative graphene oxide, with bacteria has been extensively studied, but there remains substantial controversy in this field. There have been some indications of bactericidal effects of solutions and the like having graphene flakes therein, such as in: Hu, W. et al. Graphene-based antibacterial paper, ACS Nano 4, 4317-4323 (2010); Liu, S. et al. Antibacterial activity of graphite, graphite oxide, graphene oxide, and reduced graphene oxide: Membrane and Oxidative Stress, ACS Nano 5, 6971-6980 (2011); and Tu, Y. et al. Destructive extraction of phospholipids from *Escherichia coli* membranes by graphene nanosheets, Nat.

Nanotechnology 8, 594-601 (2013). Lateral flake size of graphene oxide seems to be a relevant factor, with larger flakes having a capacity to wrap around bacterial cells, as discussed in: Liu, S. et al. Lateral dimension-dependent antibacterial activity of graphene oxide sheets, Langmuir 28, 12364-12372 (2012); and Perreault, F., de Faria, A. F., Nejati, S. & Elimelech, M. Antimicrobial properties of graphene oxide nanosheets: why size matters, ACS Nano. 9, 7226-7236 (2015). However, there are also studies demonstrating that graphene and graphene oxide have no negative effects on bacteria, and can even stimulate bacterial growth or specific metabolic functions, as discussed e.g. in: Ruiz, O. N. et al. Graphene oxide: a nonspecific enhancer of cellular growth, ACS Nano 5, 8100-262 8107 (2011); Ren, W., Ren, G., Teng, Y., Li, Z. & Li, L. Time-dependent effect of graphene on the structure, abundance, and function of the soil bacterial community, J. Hazard. Mater. 297, 286-294 (2015); and Wang, D., Wang, G., Zhang, G., Xu, X. & Yang, F. Using graphene oxide to enhance the activity of anammox bacteria for nitrogen removal, Bioresour. Technol. 131, 527-530 (2013).

It has now been found by the present inventors that the orientation of graphene in contact with bacteria is a major factor behind this controversy. In most previous studies, graphene or graphene oxide flakes of various sizes were suspended in solution, and the interaction with bacteria was therefore random and ill-defined. In such systems it is difficult to control the flake size distribution, which may cause problems with reproducibility.

In experimental tests it was found that when coating a supporting substrate with graphene in two distinctly different and strictly controlled geometries, the effect on bacteria was diametrically opposite. In coatings/surfaces where the graphene flakes/sheets was horizontal, i.e. lying in line with the surface, the coating/surface did not harm either bacterial cells or mouse fibroblasts, suggesting low risk of cytotoxicity. However, in coatings/surfaces where the graphene flakes were standing, i.e. arranged vertically, and in particular as a dense array of graphene flakes grown perpendicularly to the basal plane, the coating/surface caused extensive structural damage to bacterial cells and effectively prevented biofilm attachment to the coated surfaces. However, surprisingly, it did not induce any significant damage to mouse fibroblasts. It was therefore concluded that standing, vertically deposited Angstrom scale flakes might therefore be effectively used in prevention of bacterial infections and biofouling.

In liquid phase systems, graphene or its derivatives are suspended in solution, thereby having no constraint on the orientation of contact with the bacterial cells. Graphene and graphene oxide flakes in suspension typically exhibit large variability in terms of size, purity, level of oxidation and thickness of flake aggregates (multi-layered graphene). All of these properties vary dramatically depending on the different types of synthesis methods that have been used. The use of graphene flakes in solution is critically limited by the risk associated with free diffusion in the body, in case of medical applications, or the environment, in case of biotechnology and anti-biofouling applications.

However, Angstrom scale flakes, e.g. of graphene or graphite, attached to the surface of a substrate in a standing position, in the form of a stable coating or surface, represent a viable alternative with a broad spectrum of applications.

It has also been found that this antibacterial effect is mechanical. Without wanting to be bound by any theory, it is assumed that the sharp edges of the Angstrom scale flakes are able to come in contact and penetrate a layer of membrane lipids by forming strong van der Waals attractions. This leads to the membrane rupture, because the lipid hydrophobic tails of the membrane lipids get spread out on the Angstrom scale flake surface, attracted by strong hydrophobic interactions.

The reason that eukaryotic cells are not killed in the same way is assumed, again without wanting to be bound by any theory, to be due to the larger size of eukaryotic cells compared to prokaryotic cells, and/or the thicker walls/membranes of eukaryotic cells.

Eukaryotic cells are generally about 10 times as big as prokaryotic cells. Prokaryotic cells are generally of a size within 1-10 μm. Most bacteria are smaller than 1 μm in at least one dimension, but can be elongate and somewhat longer, up to 10 μm in a length direction. The thickness of the cell membrane varies somewhat between various cells, but is typically about 10 nm for Gram-negative bacteria, but can be 20-80 nm for Gram-positive bacteria, if including the rather thick layer of peptidoglycan. Eukaryotic cells are generally of a size within 10-100 μm.

Graphene and thin graphite are, similar to many other 2D materials, strongly hydrophobic, in comparison to e.g. graphene oxide and graphite oxide, which are less hydrophobic or even hydrophilic. It is assumed that this hydrophobic nature of the Angstrom scale flakes has a beneficial effect on the killing of the bacteria.

Since the killing of the bacteria is mechanical, and attached to the surface, many of the disadvantages of known ways to provide antibacterial effects, such as the use of antibiotics, are prevented. There is for example no risk of bacteria resistance and harmful side effects.

Due to the surprising finding that the antibacterial coating/surface with Angstrom scale flakes are efficient to kill and inhibit growth of prokaryotic cells, i.e. bacteria and the like, and the equally surprising finding that it does not kill eukaryotic cells, the coating/surface can also be used in direct contact with skin and tissue of humans and animals, without any negative or detrimental effects.

The Angstrom scale flake may be of graphene, or other 2D materials, i.e. having a thickness of only one atom layer, which corresponds to about 0.34 nm. However, the Angstrom scale flake may also be somewhat thicker, and still provide the beneficial effects discussed above. For example, the flake may comprise several layers of graphene. Thus, the Angstrom scale flakes may have a thickness in the range of 1-10 atom layers, and preferably 1-5 atom layers, and most preferably 1-3 atom layers. The thickness may be in the range 1-100 Angstrom (0.1-10 nm), and preferably 3-50 Angstrom (0.3-5 nm), and more preferably 3-20 Angstrom (0.3-2 nm), and most preferably 3-12 Angstrom (0.3-1.2 nm).

The Angstrom scale flakes may extend from the surface with a height in the range 1-1000 nm, and preferably in the range 5-500 nm, and most preferably in the range 10-100 nm. Within these ranges, there is a particular good balance between killing of prokaryotic cells and saving of eukaryotic cells.

The distance between any adjacent Angstrom scale flakes may be less than 10 μm, and preferably less than 5 μm, and most preferably less than 1 μm. Since this is in correspondence with the size of prokaryotic cells, the killing effect hereby becomes more efficient.

The distance between any adjacent Angstrom scale flakes may be more than 0.01 μm, and preferably more than 0.05 μm, and most preferably more than 0.1 μm. Since the killing effect may be reduced in case the flakes are arranged too densely, a less dense arrangement may often be preferred.

The thickness of at least some of the Angstrom scale flakes, and preferably all the Angstrom scale flakes, may be tapering towards the free end, opposite the attached edge side. Additionally or alternatively, the width of at least some of the Angstrom scale flakes, and preferably all the Angstrom scale flakes, may be tapering towards the free end, opposite the attached edge side. Hereby, the attachment to the surface may be stronger, and the killing of bacteria becomes more efficient.

The antibacterial coating/surface of the disclosed technology is useful for many different types of devices.

In one embodiment, the device may be a medical device, such as a catheter, medical tube, irrigation device or implant. In particular, the antibacterial coating/surface is well suited for medical devices which are to be used many times, such as irrigation devices, and/or for a long time, such as indwelling urinary catheters, so-called Foley catheters. In catheters, the antibacterial coating/surface may be arranged either on an internal surface, inside the lumen, and/or on an external surface. In an irrigation device, the antibacterial coating/surface may be arranged in the probe, internally and/or externally, but may additionally or alternatively be provided internally in tubes of the device, such as tubes leading irrigation liquid to the probe for irrigation. In implants, the coating/surface may e.g. be arranged close to surrounding tissue, thereby improving and speeding up the tissue healing after having inserted the implant, and reducing the need for antibiotic drugs. The implant, may e.g. be a dental implant, but may also be other types of implants.

In one embodiment, the device may form an internal lumen, and wherein said antibacterial coating/surface is arranged on an internal surface of the substrate facing said lumen.

Thus, the device may e.g. be a tube or having a generally tubular shape. For example, the coating/surface may be arranged in tubes or pipes for transporting water, thereby reducing the amount of bacteria in the water, tubes and pipes for transporting beverages, medical tubing, catheters, and the like.

Further, the device may be, or forms part of, a cell growing or cell culture equipment. Hereby, the use of antibiotic drugs, which is today commonplace, could be omitted or at least strongly reduced. Since the antibacterial coating/surface kills prokaryotic cells but without harm to eukaryotic cells, the coating/surface efficiently kills bacteria without affecting the cultured eukaryotic cells. Hereby, cells, such as skin cells, stem cells, etc, can be grown and cultured more efficiently, and with reduced negative side effects, both on the cells themselves and on the environment.

The substrate may be made of any suitable material, such as metal etc. In one embodiment, the substrate is made of a plastic material, and preferably a polymer.

For example, the substrate can be made of: polyurethanes, latex rubbers, silicon elastomers, other rubbers, polyvinylchloride (PVC), other vinyl polymers, polyesters, polyacrylates, polyamides, polyolefines, thermoplastic elastomers, styrene block copolymers (SEBS), or polyether block amide (PEBA), and combinations of these. Such substrate materials are e.g. suitable for applications such as catheters.

However, many other substrate materials may also be used, such as metals and the like. For use as implants, the substrate material may also e.g. comprise zirconia or titanium.

The substrate is preferably formed into its desired final shape prior to being coated or provided with the antibacterial surface, and may e.g. be formed by means of extrusion, co-extrusion or molding, such as injection molding, or other melt forming processes.

According to another aspect of the present invention, there is provided a method for producing an antibacterial device, comprising the steps:

providing a substrate;

providing an antibacterial coating or antibacterial surface on a surface or a part of a surface of the substrate, wherein said antibacterial coating/surface comprises Angstrom scale flakes, preferably of graphene or graphite, the Angstrom scale flakes being arranged in a standing position on said surface, and attached to the surface via edge sides thereof.

Hereby, similar properties and advantages as discussed above in relation to the other aspects of the invention are obtainable.

The attachment of the Angstrom scale flakes to the surface may be made by at least one of: spray coating, reduction of graphene oxide or graphite oxide, lamination and growing, preferably by chemical vapor deposition.

These and other aspects of the inventive concept will be apparent from and elicited with reference to the embodiments described hereinafter.

BRIEF DESCRIPTION OF THE DRAWINGS

By way of example, embodiments of the invention will now be described with reference to the accompanying drawings in which:

FIGS. 7a and 7b are diagrams showing inhibition of adhesion of *E. coli* and *S. epidermidis*, respectively, according to example embodiments;

DESCRIPTION OF PREFERRED EMBODIMENTS

Figure 1A:
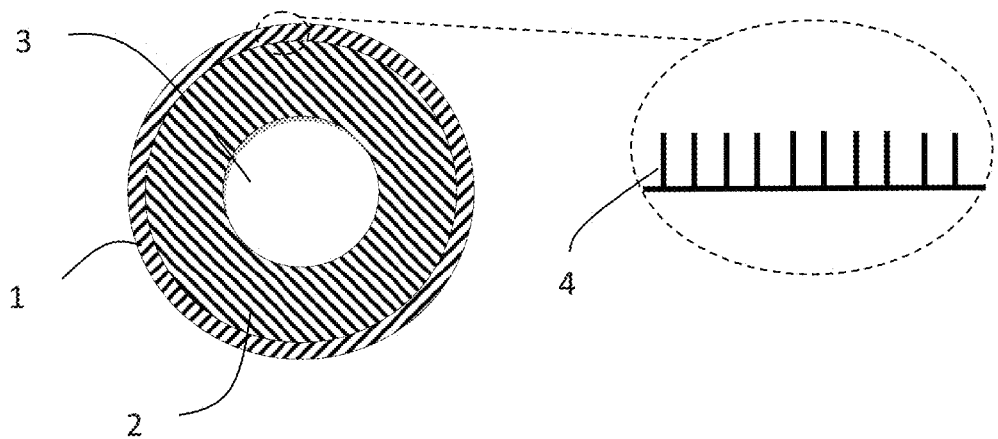
FIGS. 1a and 1b schematically illustrate examples of devices coated with antibacterial coating/surface in accordance with some embodiments.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention.

In the embodiment illustrated in FIGS. 1a, b, an antibacterial coating/surface 1 is arranged on a surface or a part of a surface of a substrate 2. The substrate is here in the form of a tube, with an internal canal or lumen 3. The antibacterial coating/surface comprises Angstrom scale flakes 4 of graphene or graphite, arranged in a standing position on said surface and attached to the surface via edge sides thereof. In the example of FIG. 1a, the antibacterial coating/surface is arranged on an external surface of the tube, whereas the antibacterial coating/surface in FIG. 1b, is arranged on an internal surface of the tube.

The antibacterial coating/surface may be arranged along the entire length of the tube, or over only a part of the length. Further, the antibacterial coatings/surfaces may be arranged on both the inside and the outside of the tube.

Figure 1B:
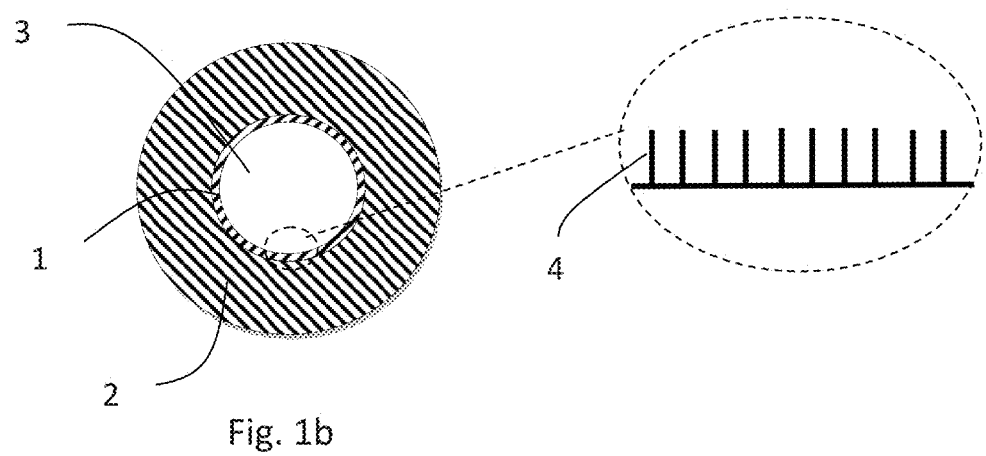

The tube of FIG. 1a and FIG. 1b may be used for transfer of many types of different gases and liquids, and may be used for many type of applications, such as in food processing industries, in medical devices, etc.

In one example, the tube is a medical tube for transfer of irrigation liquid in an irrigation system, e.g. of the type disclosed in U.S. Ser. No. 13/911,125, U.S. Ser. No. 13/929,312, U.S. Ser. No. 13/929,213 and U.S. Ser. No. 13/929,091 by the same applicant, said documents hereby being incorporated in their entirety by reference.

The tube may also form part of catheter, thereby e.g. forming the whole or a part of the elongate shaft. In particular, the catheter may be a urinary catheter, and preferably a urinary catheter for long time use, a so-called Foley catheter. The catheter preferably comprises a closed, rounded insertion tip arranged at an insertion end of the elongate shaft, a drainage inlet opening arranged at or adjacent the insertion tip, and a drainage outlet opening arranged at the opposite end of the elongate shaft. The catheter may further comprise a retention member, such as an inflatable balloon, for maintaining the catheter in place during use. Further, the catheter may comprise an enlarged, and preferably flared, rearward end for connecting the catheter, and the drainage outlet, to other parts, such as further tubes, a urine collection bag, or the like. The catheter may have a single internal lumen, but may also comprise two or more lumens.

At least a part of the elongate tube, and preferably the entire insertable length, may additionally be provided with a low-friction coating, such as a hydrophilic coating, and preferably arranged on an external surface of the tube.

In the above-discussed embodiments, the substrate is formed as a tube. However, the substrate may also be shaped in many other ways, such as in the form of a disc, a container, or the like.

The substrate is preferably made of a plastic material, and preferably a polymer, such as a thermoplastic elastomer or the like. However, many other substrate materials, such as metals and the like, may also be used for certain applications.

The substrate is preferably made and shaped into its intended final shape prior to being coated or provided with the antibacterial surface. The forming may e.g. be obtained by extrusion or injection molding.

Examples and Experiments

In order to establish well-defined interaction conditions between bacteria and graphene, two supporting surfaces, silicon dioxide (SiO2) and gold (Au), were coated with graphene in two distinct and strictly controlled geometries.

In two examples, Ex A and Ex B, a vertical coating was provided, as a relatively dense array of standing graphene flakes grown perpendicularly to the basal plane, with a typical height of 60-100 nm on two different substrates.

As comparative examples, Comp Ex A and Comp Ex B, a horizontal coating was provided as a single sheet of monolayer CVD graphene, deposited on the same substrates.

The reason for using two reference surfaces was that SiO2 is insulating and Au is conductive, and thus to test whether conductivity of the coated surface could have any effect.

For the horizontal coating, Comp Ex A and Comp Ex B, a single layer of chemical vapor deposition (CVD) graphene was synthesized on copper foil, and transferred onto SiO2 and Au surfaces (6×6 mm plates), using poly-methyl methacrylate (PMMA) as support during transfer. The coating process generally followed the method disclosed in Li, X. et al. "Large-area synthesis of high-quality and uniform graphene films on copper foils", Science 324, 1312-1314 (2009).

For the coating with the standing flakes, Ex A and Ex B, samples of SiO2 and Au coated with graphene flakes aligned perpendicular to the surface were prepared, produced by plasma enhanced chemical vapor deposition (PECVD), generally using the technique disclosed in Liu, L. et al. "A mechanism for highly efficient electrochemical bubbling delamination of CVD-grown graphene from metal substrates" Adv. Mater. Interf. 3, 1500492 (1-10) (2016). This method allows for controlling the size, thickness, density, orientation and even in situ doping of vertically oriented Angstrom scale flakes, rooted in the coated substrate.

More specifically, the SiO2 substrate used in the examples was a standard p-type silicon wafer with 400 nm thick SiO2 film prepared by wet oxidation using oxyhydrogen at 1050° C. For the Au substrate, the wafer was deposited with a 400 nm thick Au film by electron beam evaporation. After loading the wafer to the cold wall CVD system, the samples were rapidly heated (~300° C./min) to the growth temperature of 775° C. and annealed in H2 and Ar atmosphere. A 75 W DC glow-discharge plasma was ignited and the graphene growth was initiated by introducing 15 sccm C2H2, 15 sccm H2 and 1000 sccm Ar.

Figure 2A:
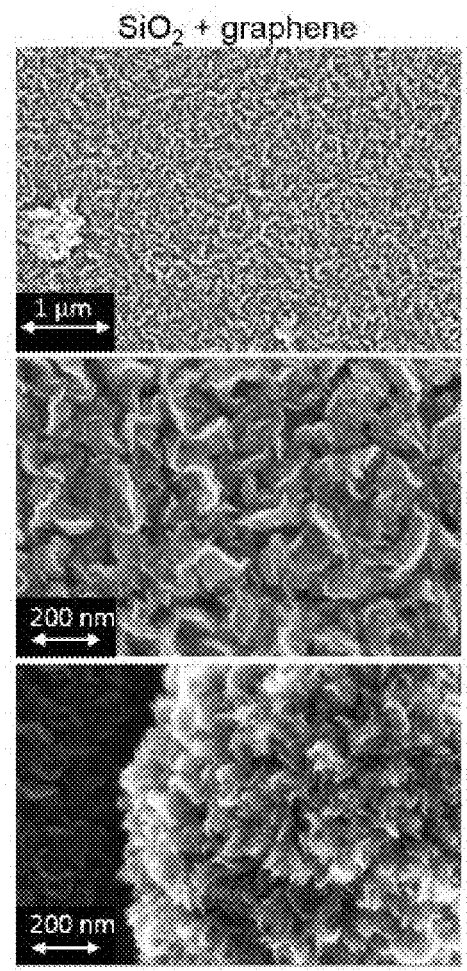
FIGS. 2a and 2b are SEM pictures of coated surfaces prepared in accordance with some embodiments.
Figure 2B:
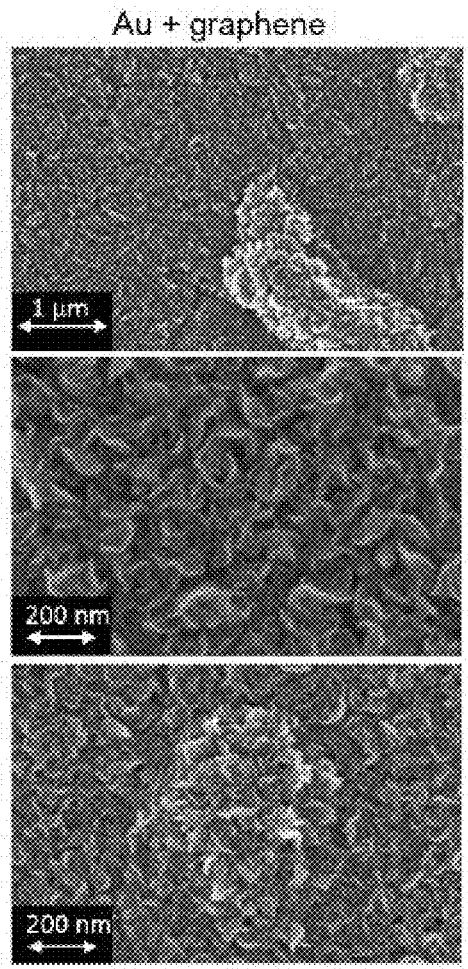

Examples of such surface coated with standing Angstrom scale flakes is shown in FIGS. 2a and 2b, showing the coatings on SiO2 substrate and Au substrate, respectively. Images with low magnification are at the top, and high magnification at the bottom, and all images are viewed from above. Because the graphene is quasi-suspended, a small acceleration voltage (5 kV) was used for observation of surface features. The scanning electron microscopy (SEM) images of the surface, FIGS. 2a and 2b, reveal the regular structure of vertically aligned graphene Angstrom scale flakes.

Figures 3A, 3B:
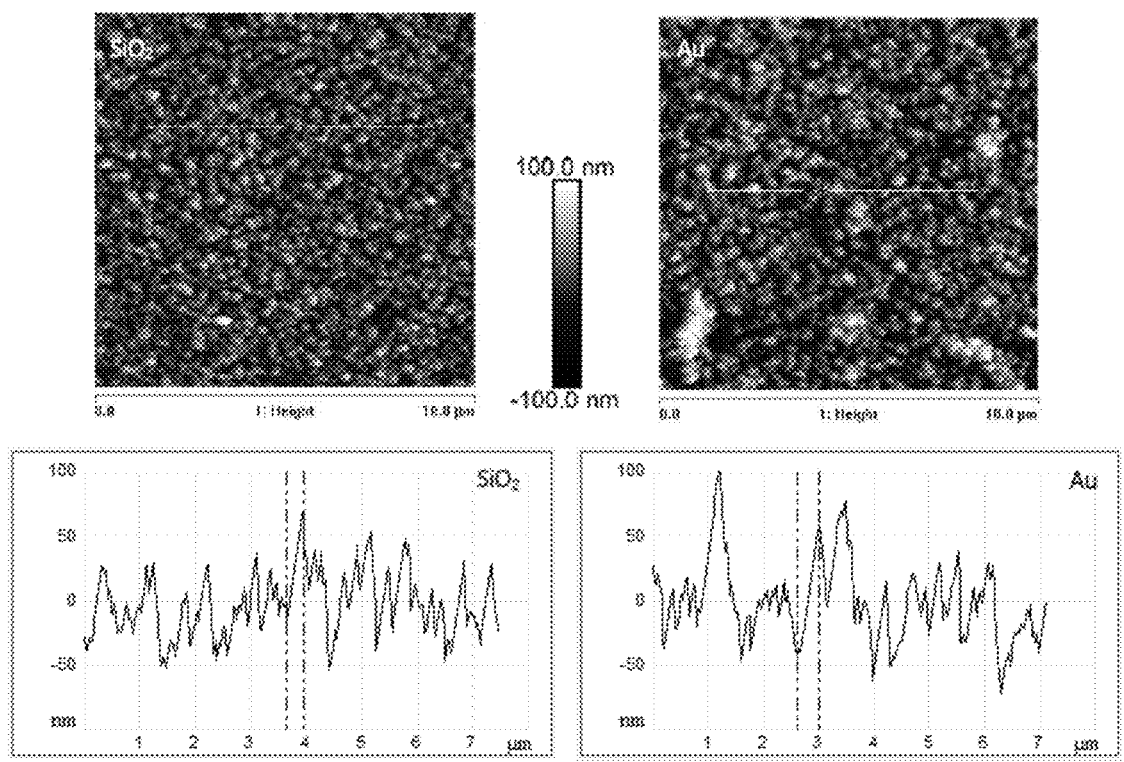
FIGS. 3a and 3b are AFM pictures of the coated surfaces of FIGS. 2a and 2b, respectively, and corresponding diagrams showing cross-sectional profiles along lines of said coated surfaces.

The dimensions of the Angstrom scale flakes were determined using atomic force microscopy (AFM), as shown in FIGS. 3a, b. The horizontal white lines in the images correspond to the cross-sectional profile analyzed for flake height, as shown in the diagrams beneath each image. The analysis indicated that the flakes had an average size of 60 nm on the SiO2 substrate and 100 nm on the Au substrate.

Figure 4A:
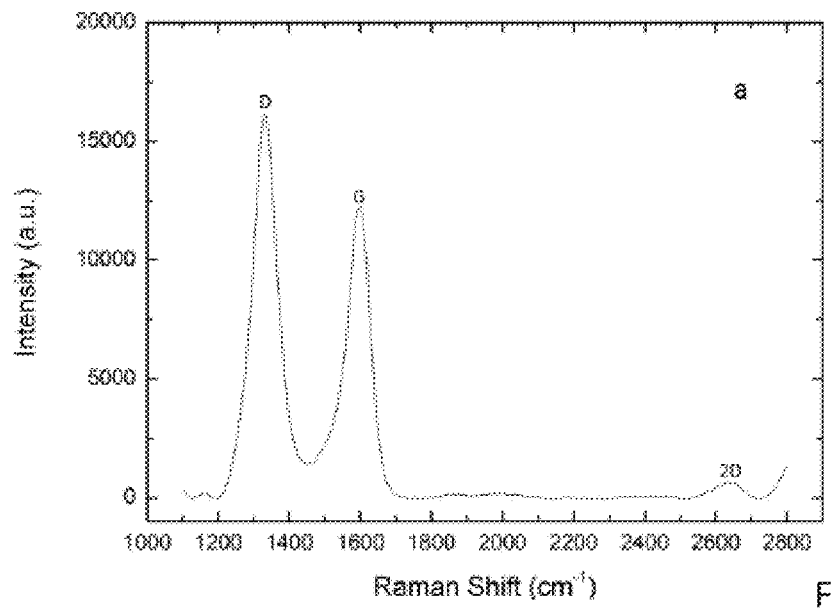
FIGS. 4a and 4b are Raman spectra of the coated surfaces of FIGS. 2a and 2b, respectively.
Figure 4B:
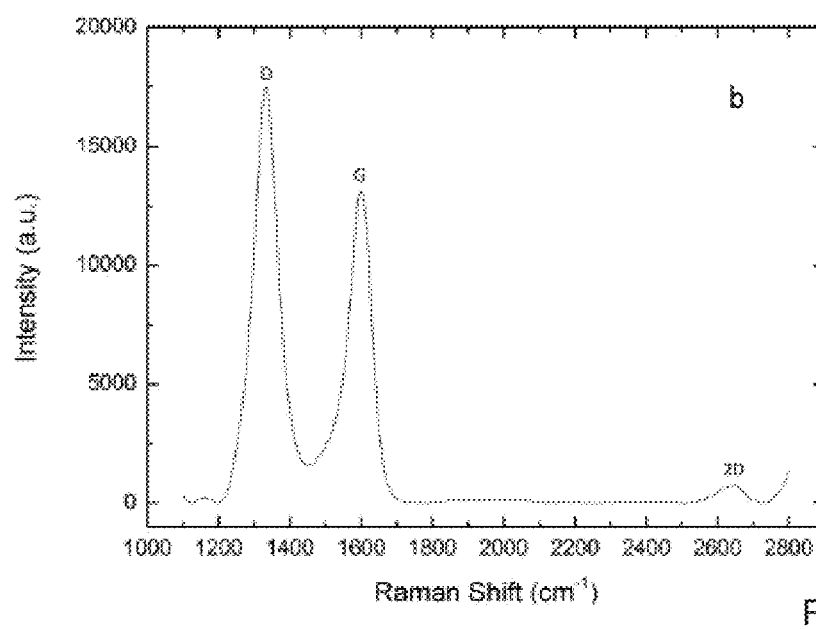

The samples were also analyzed with Raman spectrometry analysis. FIGS. 4a and 4b show Raman spectra of coated SiO2 and Au substrates, respectively. The laser wavelength was 638 nm. The three main characteristic Raman peaks for graphene, D, G and 2D are all detected. The D peak (at about 1350 cm−1) implies disorders, the G peak (at about 1590 cm−1) is related to the sp2 C—C bond, and indicates the degree of graphitization, and the 2D peak (at about 2650 cm−1) intensity declines with the increasing number of graphene layers and decreasing lattice quality. Due to the vertical structure and the large amount of flake boundaries, the D band is high compared to the G band. A small 2D peak is observed, indicating that the samples are a mixture of monolayer and multilayer graphene. Taking into account the SEM results (FIGS. 2a, b) it is estimated that the number of layers is on average less than 10. This result confirms the graphite structure of the samples, and an adequate quality. As a comparison, in many liquid phase-derived graphene nanoflakes, the 2D peak is completely absent due to a large number of defects. Thus, the Raman spectrometry analysis confirmed the graphitic structure of the samples and their comparably good quality.

The anti-bacterial effect of the coated substrates was then tested.

Gram-negative *Escherichia coli* (UTI89) and Gram-positive *Staphylococcus epidermidis*, causative agents of urinary tract infections and infections related to implants and catheters, were used to test the antibacterial properties of the coatings. Many past studies have examined the effect of graphene on planktonic bacteria, which is not the most common condition for bacterial cells in their natural environment. Therefore, it was instead decided to examine the effect on bacterial biofilms, since these protected, multicellular structures are much more relevant in the context of bacterial infections and biofouling.

To test the anti-bacterial effect, bacterial biofilms were grown directly on the analyzed surfaces. Bacterial inoculum (2×105 Colony Forming Units (CFU) of overnight culture) was deposited on top of the coated surfaces, where it was left to form a biofilm. The biofilm was incubated for 72 h, harvested, sonicated, and the surviving bacteria were counted as CFU on agar plates.

Figures 5A, 5B:
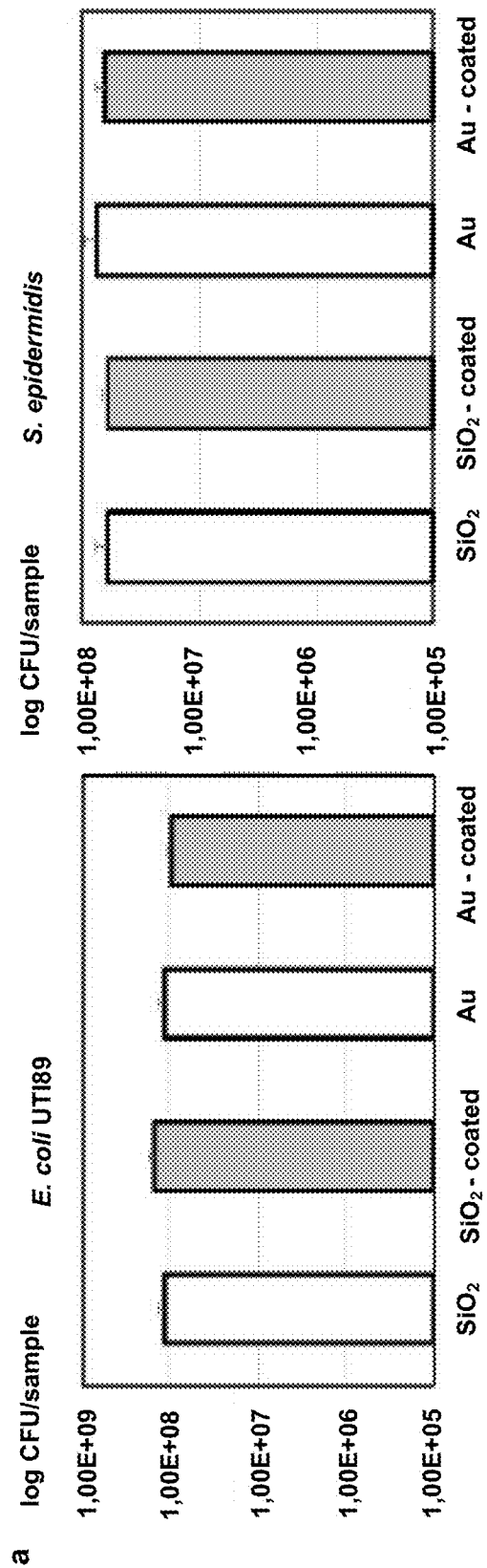
FIGS. 5a and 5b are diagrams showing the CFU count for comparative examples.

First, the coated surfaces of Comp Ex A and Comp Ex B were tested, and compared with uncoated surfaces of the same substrate materials (SiO2 and Au). It was found that monolayer graphene deposited on either SiO2 or Au surfaces had no measurable effect on the CFU counts of *E. coli* or *S. epidermidis* in the 72-hour biofilm, as shown in the diagrams of FIGS. 5a and 5b, where FIG. 5a relates to *E. coli* UTI89 and FIG. 5b relates to *S. epidermidis*. The grey bars are the coated substrates, with horizontal monolayer graphene coatings, in accordance with Comp Ex A and Comp Ex B, whereas the white bars are substrates without coating. Error bars represent the standard deviation from three independent biological replicates. It was concluded that horizontal monolayer graphene coatings had no impact on bacterial attachment or survival.

Figures 6A, 6B:
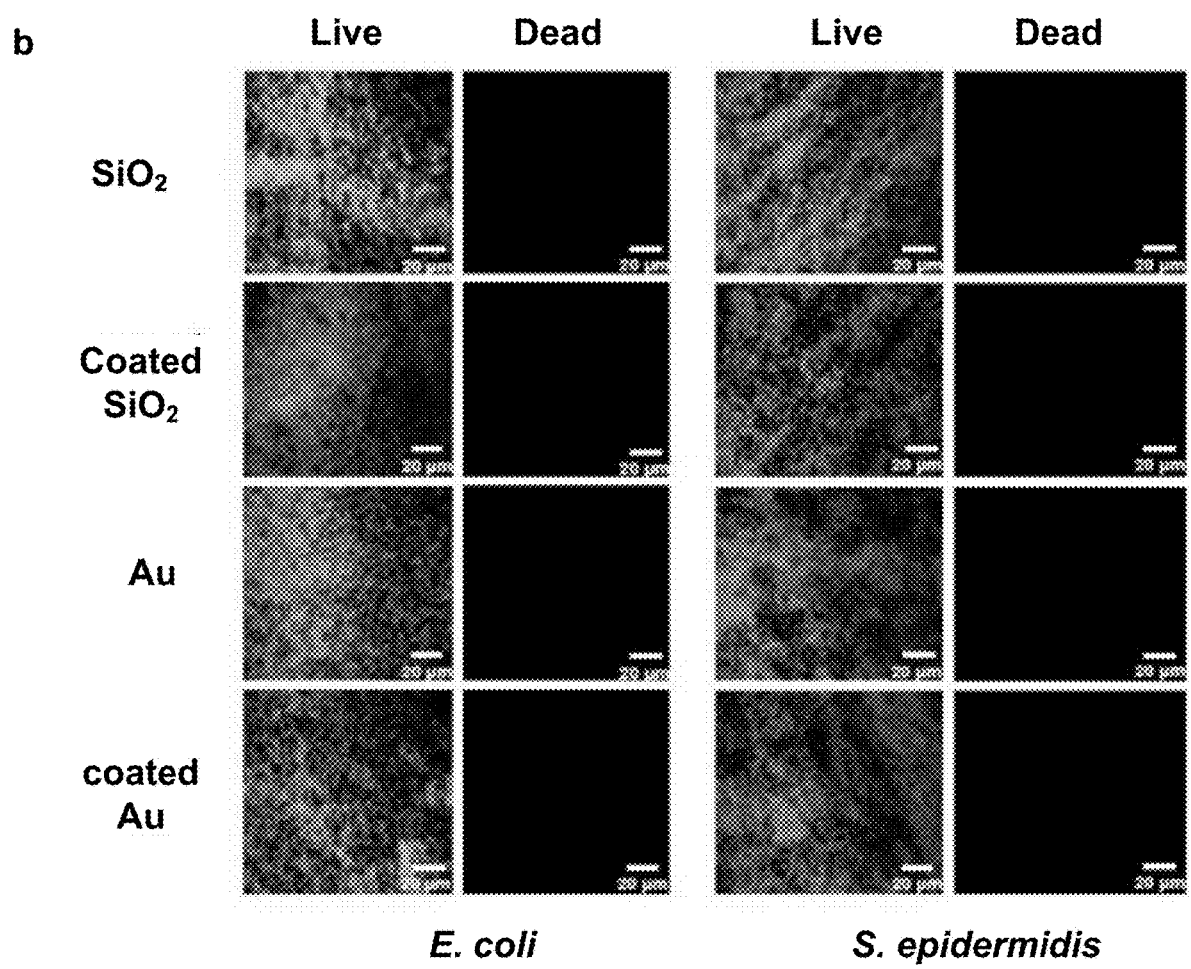
FIGS. 6a and 6b are images showing live and dead staining of *E. coli* and *S. epidermidis*, respectively, in comparative examples.

To verify this with an independent method, the live/dead bacterial cells were visualized with propidium iodide staining. Propidium iodide enters and stains dead cells, but cannot permeate live cells. The result of this experiment is shown in FIG. 6a, related to *E. coli*, and FIG. 6b, related to *S. epidermidis*. Live bacterial cells are shown in the images of the left-hand columns as green (here grey) areas. Dead bacterial cells are shown in the images of the right-hand columns as red (here grey) areas. Similar patterns and amounts were found on all the samples. No dead cells were identifiable. Thus, this test confirmed the finding obtained by the CFU counts, viz. that the horizontal graphene coating had no adverse effects on either bacterial strain.

Corresponding measurements were then made on the substrates coated with the vertical flakes of Ex A and Ex B.

At first, the effect of these surfaces on adhesion of *E. coli* and *S. epidermidis* biofilms was tested. The result is shown in the diagrams of FIGS. 7a and 7b, showing the results for *E. coli* and *S. epidermidis*, respectively. Both strains were cultured for 1 h (white bars) and 4 h (gray bars) on the SiO2 and Au substrates, and both on substrates with vertically aligned graphene, in accordance with Ex A and Ex B, and on uncoated substrates, to analyze the inhibition in bacterial adhesion.

It was found that the coating containing vertically aligned graphene exhibited a strong inhibitory effect on adhesion of both bacterial pathogens, which was more pronounced for the shorter incubation interval (1 hour).

Figures 8A, 8B:
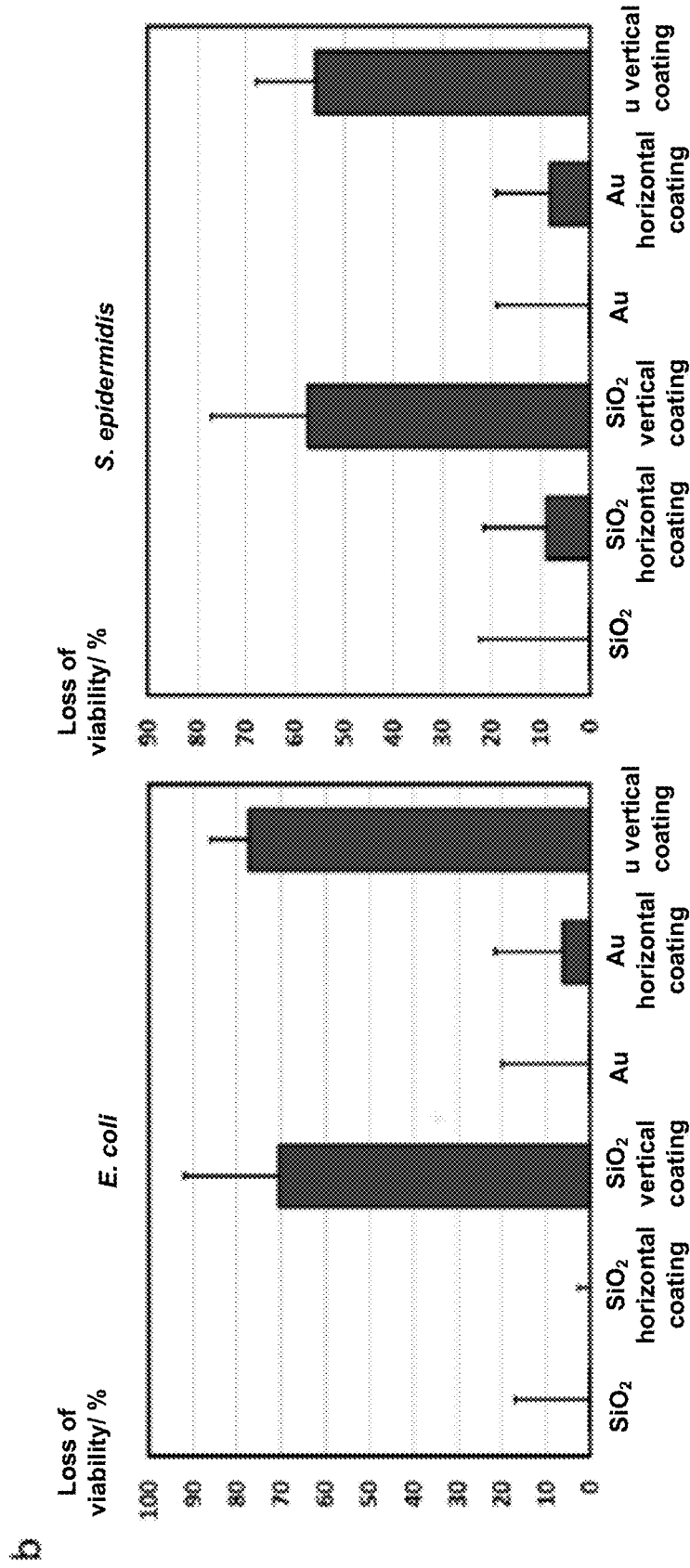
FIGS. 8a and 8b are diagrams showing loss of viability of *E. coli* and *S. epidermidis*, respectively, according to example embodiments as well as comparative examples.

Further, the impact of these surfaces on the survival of *E. coli* and *S. epidermidis*, was tested, using the exact same experimental setup (72 hour old biofilm) as for horizontal graphene described above. The result is shown in the diagrams of FIGS. 8a and 8b, related to *E. coli* and *S. epidermidis*, respectively. The diagrams show the loss of viability measured for *E. coli* and *S. epidermidis* biofilms grown on SiO2 and Au surfaces for 72 h, where the grey bars are related to coated surfaces and white bars, which are hardly visible, are related to uncoated surfaces.

In all the diagrams of FIGS. 7a, 7b, 8a and 8b, both types of graphene coatings, i.e. vertically grown in accordance with Ex A and Ex B, and horizontal monolayer in accordance with Comp Ex A and Comp Ex B, are indicated under corresponding bars. The data for horizontal monolayer coating (Comp Ex A and Comp Ex B) are the same as discussed above, in relation to FIGS. 5a and 5b, but converted to loss of viability for comparison with the vertical coating (E×A and E×B). Error bars represent the standard deviation from three independent biological replicates.

These results clearly show that coatings with standing flakes of graphene, i.e. vertically aligned graphene coating, are bactericidal. The vertically deposited graphene coating exhibited a pronounced killing effect on both bacterial species, with loss of viability ranging from 60% for *S. epidermidis* to 80% for *E. coli*. By comparison, the killing effect of the horizontal monolayer graphene (data converted from FIGS. 5a and 5b) was either nonexistent or very small. Further, the loss of viability was almost identical for Ex A, using a SiO2 substrate, and Ex B, using the Au substrate, indicating that the bactericidal effect of vertically grown graphene was not related to the conductivity of the coated surface.

Figures 9A, 9B:
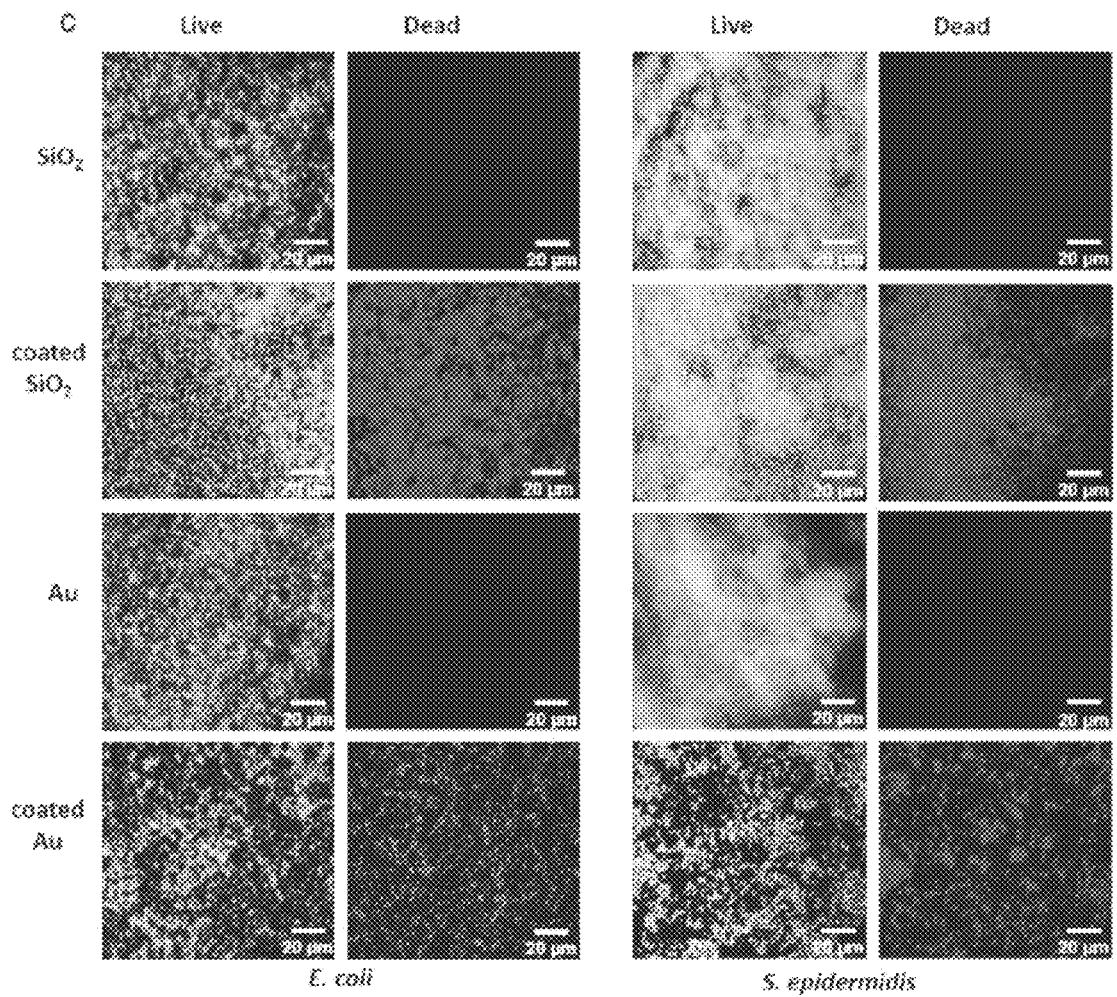
FIGS. 9a and 9b are images showing live and dead staining of *E. coli* and *S. epidermidis*, respectively, according to example embodiments.

Then, live and dead staining of *E. coli* and *S. epidermidis* was used on vertically aligned graphene-coated surfaces in accordance with Ex A and Ex B, and, as comparison, on uncoated substrates. Again, propidium iodide was used for the staining. The result of this experiment is shown in FIG. 9a, related to *E. coli*, and FIG. 9b, related to *S. epidermidis*. Live bacterial cells are shown in the images of the left-hand columns as green (here grey) areas. Dead bacterial cells are shown in the images of the right-hand columns as red (here grey) areas. The experiment was performed in three biological replicates and representative images are shown.

The propidium iodide staining of the biofilms confirmed the results of CFU counts. It revealed significant amounts of dead bacteria on the vertically coated samples (ExA and ExB), and no detectable dead bacteria on the control samples, having uncoated surfaces.

Figure 10:
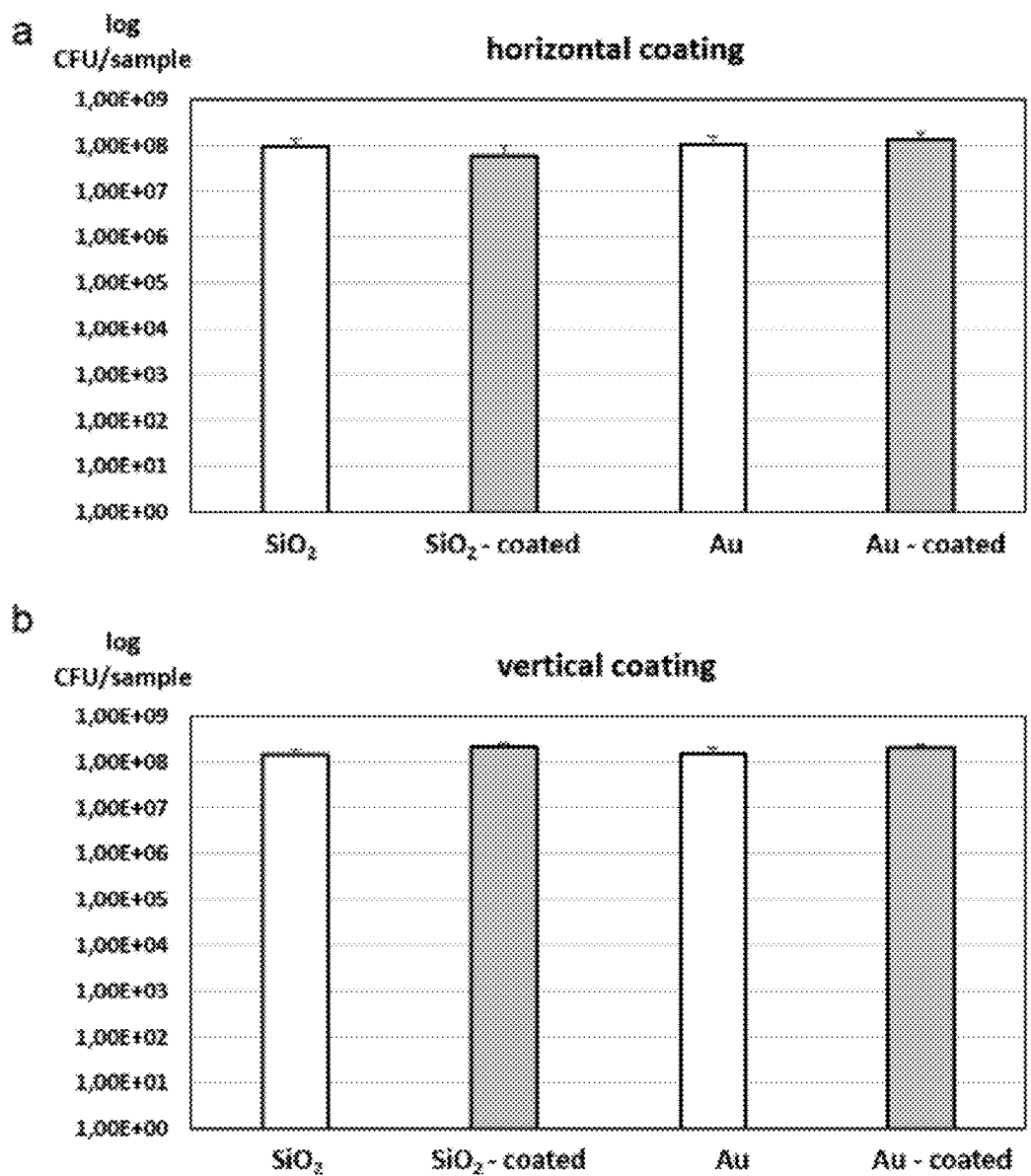
FIG. 10 are diagrams of CFU counts in liquid medium fractions used to rinse biofilms according to example embodiments as well as comparative examples.

To assess whether the coating had any effect on the mechanical stability of the biofilm, CFU counting was carried out with rinsing fractions, performed on the biofilm samples every 24 h to replenish the growth medium. The result is shown in the diagrams of FIG. 10, where the top diagram shows coated substrates with horizontal graphene, in accordance with Comp Ex A and Comp Ex B as grey bars, and control measurements on substrates without coatings as white bars, and the lower diagram shows coated substrates with vertical graphene, in accordance with Ex A and Ex B as grey bars, and control measurements on substrates without coatings as white bars. The numbers of bacteria released from the biofilm during the washes were identical in all samples. From this is was concluded that the measured loss of bacterial viability in Ex A and Ex B was not due to mechanical destabilization of the biofilm, since the biofilm rinsing fractions contained the same CFU counts for all tested surfaces.

It was therefore concluded that vertically aligned graphene coating exhibits bactericidal effects and prevents attachment of bacterial biofilms.

Figure 11A:
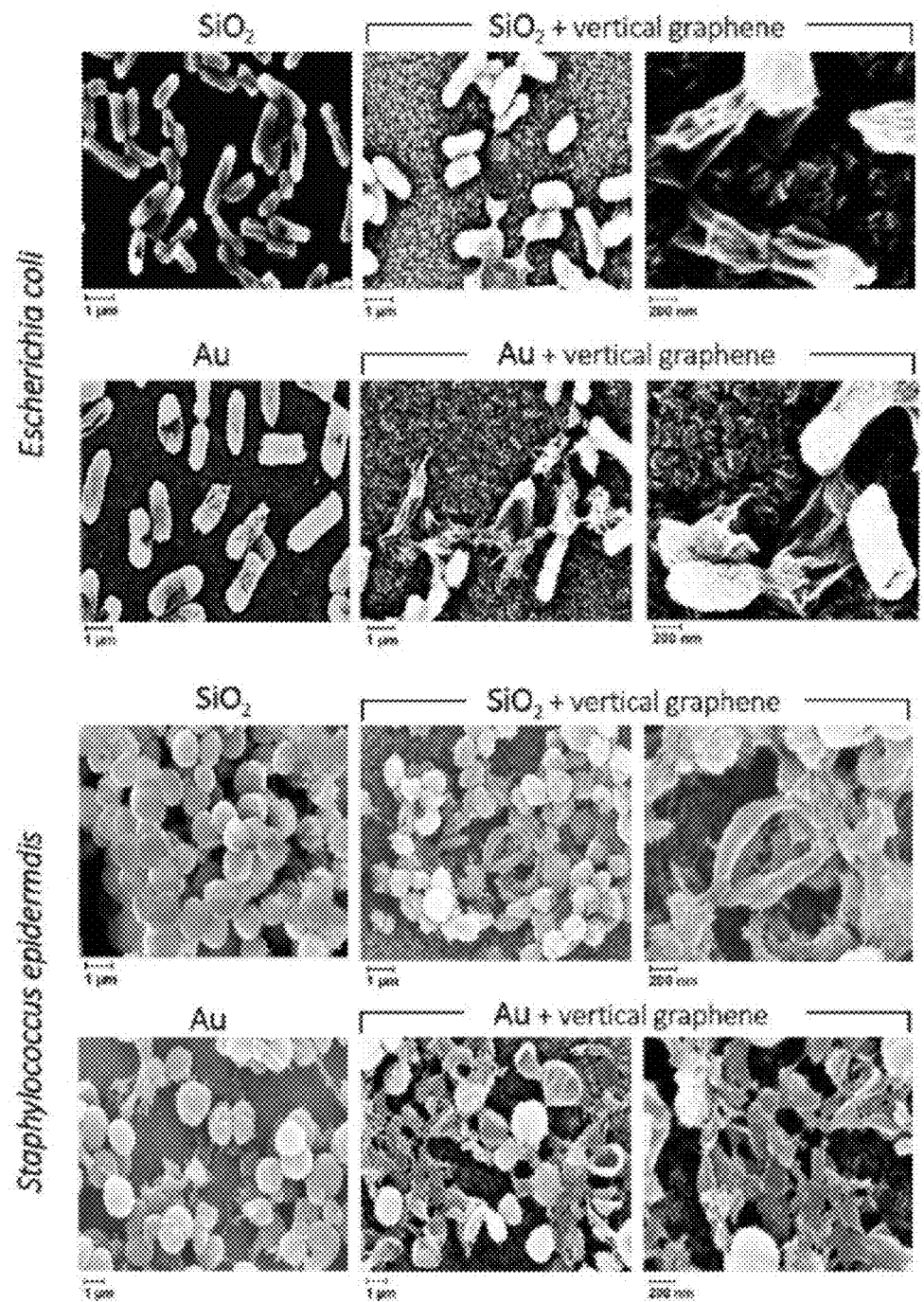
FIG. 11a is SEM images if bacteria on coated according to example embodiments as well as comparative examples.
Figure 11B:
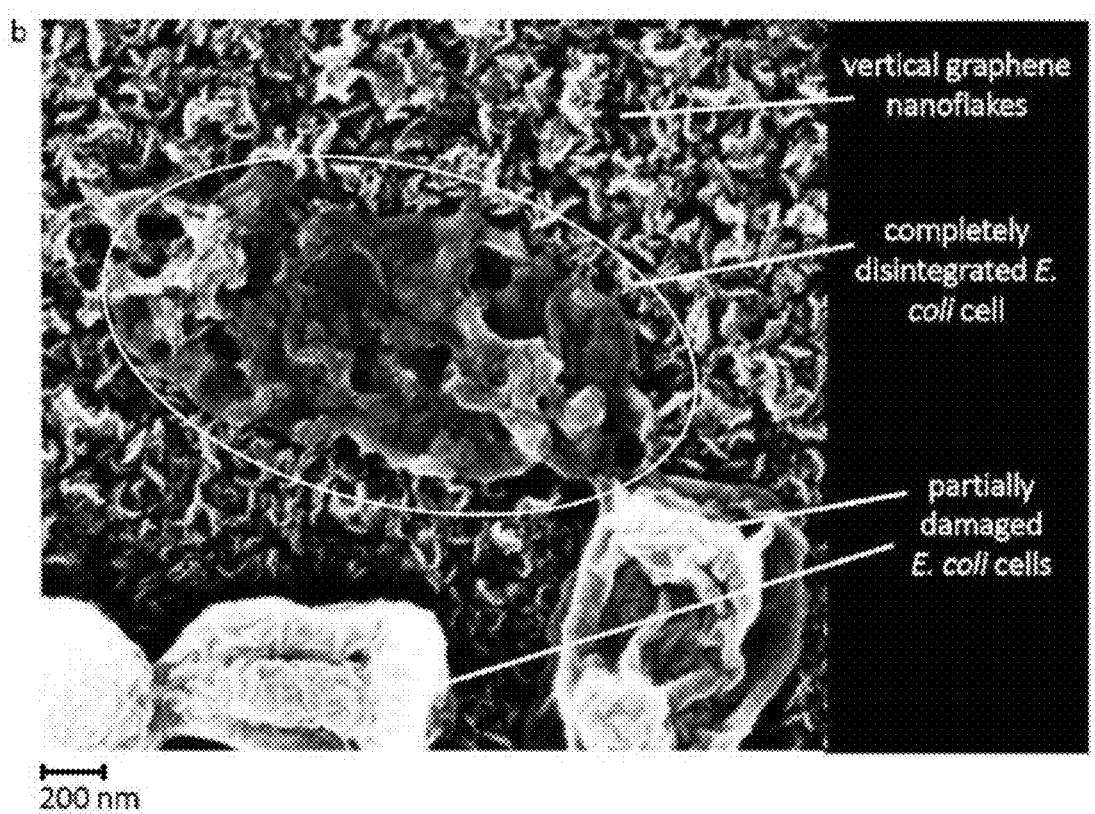
FIG. 11b is a high magnification image of damaged cells.

In order to explore the mechanism by which bacterial viability and attachment are reduced on the vertically coated surfaces, the morphology of the cells was examined with SEM. The result is illustrated in FIGS. 11a, b. In the images of FIG. 11a, the two top rows show SEM images of *E. coli* and the two bottom rows show SEM images of *S. epidermidis*, on the SiO2 surfaces (rows 1 and 3) and Au surfaces (rows 2 and 4). The images in the left-hand column are on control substrates without coating, and the images in the two right-hand columns are images of lower and higher magnification of samples coated with vertically aligned graphene, in accordance with Ex A and Ex B. The right-most images show coated samples with higher magnification. The experiment was performed in three biological replicates and representative images are shown. In FIG. 11b, there is a high magnification illustrative image of *E. coli* cells on the coated surface, showing a completely disintegrated cell, and several partially damaged cells.

From FIGS. 11a, b, the following may be noted and concluded: The *E. coli* and *S. epidermidis* cells maintained their full envelope integrity on the non-coated SiO2 and Au controls. On the contrary, morphological changes, consistent with cell disintegration, were observed with the bacterial cells on surfaces vertically coated with graphene, i.e. on the examples in accordance with Ex A and Ex B. The zoomed-out images show a heterogeneous picture, with some cells entirely disintegrated, some damaged and some seemingly intact. The zoomed-in images of *E. coli* cells reveal large surfaces of broken cellular envelopes stretched on the graphene surface. For *S. epidermidis*, which appeared more resistant to graphene in loss of viability and propidium iodide assays, the damage of the envelope seemed to be more contained, and on average fewer cells were affected. The damage in both cases appeared to be mechanical. Presumably, the sharp edges of graphene are able to come in contact and penetrate a layer of membrane lipids by forming strong van der Waals attractions. In the above-related experiments this leads to the membrane rupture, because the lipid hydrophobic tails of the membrane lipids get spread out on the graphene surface, attracted by strong hydrophobic interactions. This killing mechanism becomes active when the lipid hydrophobic tails come in direct contact with graphene, i.e. an exposed sharp edge penetrates into the membrane. The observed differences in loss of viability between *E. coli* and *S. epidermidis* are most likely related to the different envelope composition of Gram-negative and Gram-positive bacteria, and differences in probability that graphene will get in direct contact with the membrane lipids. The cell wall of Gram-negative bacteria (*E. coli*) is 8-12 nm thick and contains around 20-30% of murein, which maintains the structural integrity, while in Gram-positive bacteria (*S. epidermidis*) the cell wall is approximately 20-80 nm thick, with 70-80% of murein, which makes it comparatively more robust. The stretched out membrane surfaces projected from partly disintegrated *E. coli* cells could probably correspond to fragments of the outer lipid membrane, not contained in the cell wall, and absent in *S. epidermidis*. The round shape of cocci may also contribute to its resistance to graphene penetration, because the shape reduces the bacterial surface interacting with the graphene edges upon contact. From this it is concluded that the coating having standing flakes is efficient as an anti-bactericidal coating for presumably all bacteria, but more efficient against certain bacteria than others, depending on cell wall thickness etc.

A qualitative examination of a large number of SEM images suggests that there is a positive correlation between the vertical orientation, density and sharpness of the Angstrom scale flake edges on the one side and the severity of damage to the bacterial cells on the other. The different observed degrees of damage are illustrated in FIG. 11b, showing a completely disintegrated cell, next to several cells exhibiting varying degrees of partial damage. From this, it is concluded that the dimensions, shape and density of the standing flakes are of importance for optimizing the bactericidal effect.

The disintegrated cell in FIG. 11b covers a large graphene surface. In a prolonged incubation, disintegrated cells like this one could be expected to cover large portions of the surface, and reduce the bactericidal effect. This is in perfect agreement with the observation that attachment of bacteria is more effective with prolonged incubation. However, when used in a flowing environment, such as in a tube, the stream of flowing fluid will likely clean the coated surfaces, thereby preventing or at least alleviating this reduced effect.

Next, it was evaluated whether the bacteria can develop resistance against the effect of the vertically aligned graphene. Since *S. epidermidis* showed more resistance to begin with, this strain was selected to evaluate the resistance development. First, the bacterial biofilm was incubated for 24 h on SiO2 and Au substrate with or without vertical coating. Then the bacteria were re-suspended for the survivors to recover, and re-cultured them on the new samples of the respective surfaces, for 2 more 24 h rounds. Viability of bacteria was measured for each batch.

Figure 12:
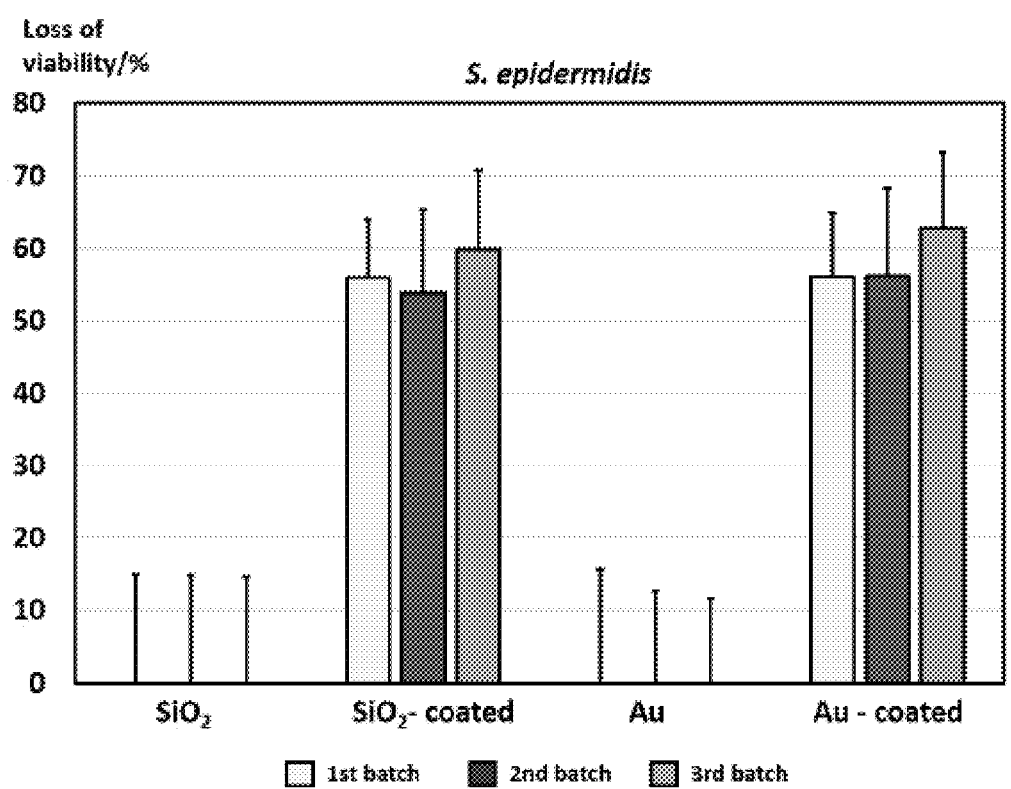
FIG. 12 is diagrams showing bacterial resistance development.

The results of these measurements are illustrated in the diagram of FIG. 12. The loss of viability was consistently the same in all re-cultured batches, indicating that no resistance to the killing effect of vertical graphene has developed. Thus, it is concluded that the anti-bacterial coating prevents emergence of bacteria resistance.

In the above-discussed experiments, *E. coli* was grown in Luria-Bertani (LB) medium and *S. epidermidis* was grown in tryptic soy broth (TSB) at 37° C., in a shaking incubator. To evaluate the effect on adhesion, overnight grown bacterial culture was diluted (½ diluted respective medium with sterile water) to make an inoculum containing $2-5 \times 10^4$ CFU/ml. 50 µl of the inoculum was placed on top of each sample (control and graphene-coated surfaces) and incubated at 37° C. and incubated for 1 h or 4 h. After the respective time of incubation, adhered bacteria was detached and homogenized by using probe sonication (10 W, for 20 s) and plated on agar plates to count colonies. In order to evaluate the antibacterial activity on matured biofilm cells (see below), the overnight grown bacterial culture was diluted to make an inoculum containing 2-5×106 CFU/ml in their respective media. 50 µl of the inoculum was placed on top of each sample (control and graphene-coated surfaces) and incubated at 37° C. Bacteria formed a biofilm on the surfaces, and the old medium was replaced with a fresh one every 24 h, until the biofilm age of 72 h. The CFUs in the old culture media was also evaluated. The 72 h biofilms were rinsed twice with sterile water and collected in 5 ml of 0.89% NaCl. The biofilms were detached and homogenized by using probe sonication (10 W, for 20 s). The homogenized suspensions were diluted serially and plated on LB and TSB agar for $E.$ $coli$ and $S.$ $epidermidis$, respectively. The colonies were counted after 24 h of incubation for $E.$ $coli$ and after 48 h for $S.$ $epidermidis$. Loss of viability percentage was calculated with respect to the control sample. To evaluate the resistance development, 24 h old $S.$ $epidermidis$ biofilms were formed on vertical graphene coated and non-coated surface by using 50 µl of inoculum containing 2-5×106 CFU/ml in TSB broth. The homogenized biofilm cells were re-cultured for 24 h on respective new coated and non-coated substrate, again the homogenized biofilm cells from second batch were re-cultured on respective new coated and non-coated substrate for 24 h. Homogenized biofilm cells from each batch was plated on TSB agar plate to evaluate the viability of bacteria. Loss of viability percentage was calculated with respect to the control sample. Each experiment was repeated at least three times, and the standard deviation reflects the results obtained in all biological replicates.

In a further study, it was examined if the vertically coated graphene surfaces would have the same deleterious effect on eukaryotic cells. This was evaluated using a cell culture of mouse fibroblasts, NIH3T3, and the result is presented in the images of FIGS. 13$a$, $b$, $c$.

The toxicity of graphene-coated surfaces for NIH3T3 cells was tested by staining the cells with a membrane integrity evaluation kit (ReadyProbes® Cell Viability Imaging Kit (Blue/Red), Thermo Scientific). Its active dyes show different specificities within viable and damaged cells, with NucBlue® Live reagent staining the nuclei of all the cells, while propidium iodide stains only the nuclei of cells with compromised membrane integrity. After growing on surfaces with and without graphene coating, as described above, the NIH3T3 cells were stained according to the kit manufacturer's instructions and fixed with freshly made 4% paraformaldehyde in DPB S for 10 min at room temperature. Graphene-coated chips were then rinsed in distilled water and mounted with a droplet of ProLong® Diamond Antifade Mountant medium (Thermo Scientific) against a glass coverslip and the back of the coverslip attached, with a small amount of superglue, to a glass slide for imaging. Imaging was performed with confocal laser scanning microscope.

Figure 13A:
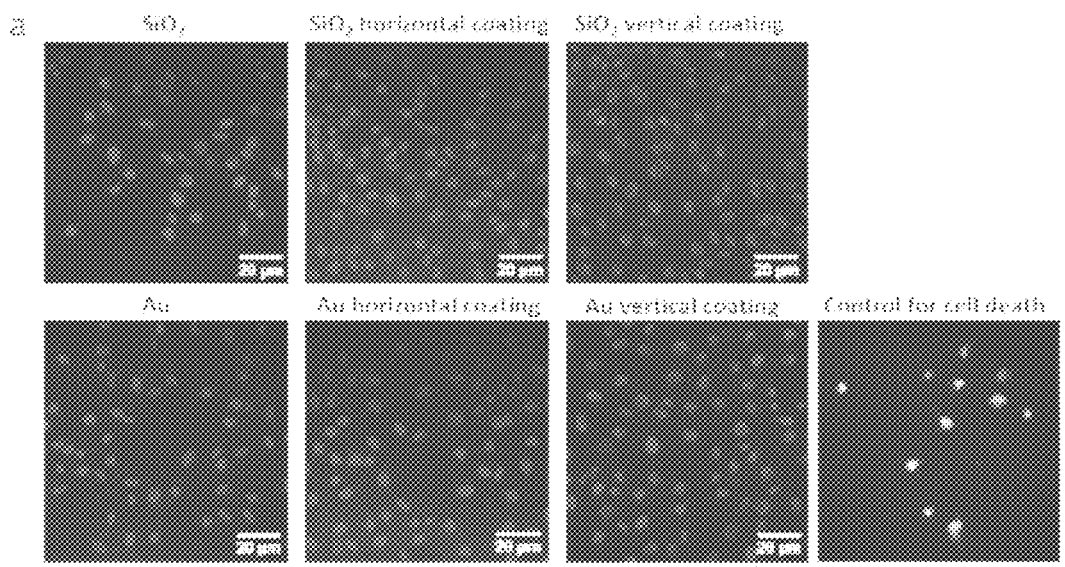
FIG. 13a is laser scanning confocal microscope images showing eukaryotic cells on coated substrates according to example embodiments.
Figure 13B:
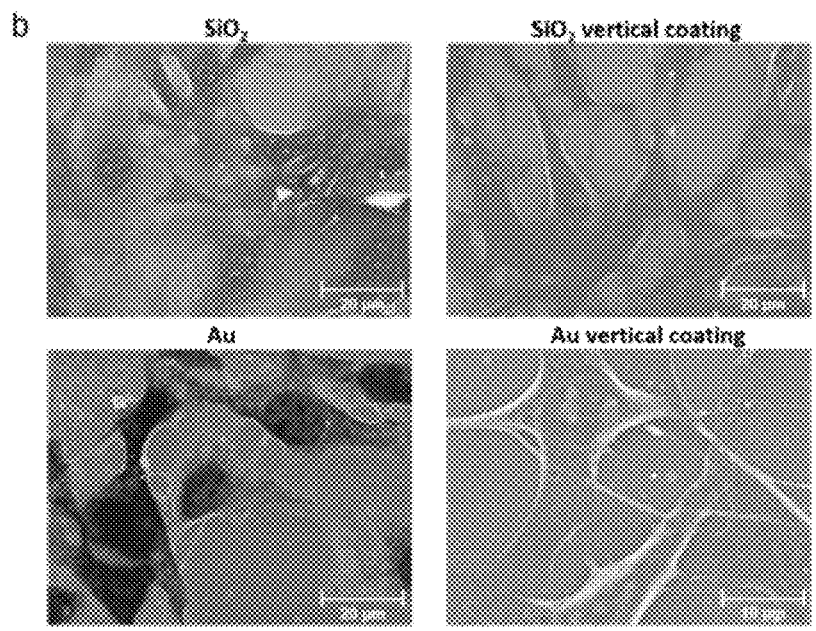
FIG. 13b is SEM images of this.
Figure 13C:
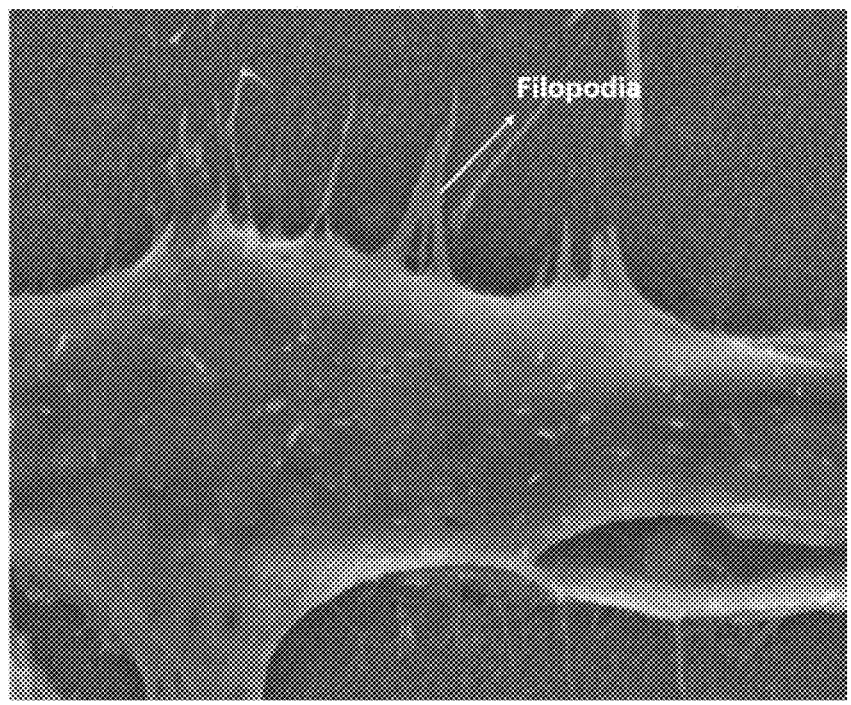
FIG. 13c is a high magnification SEM image of a cell on the coated surface, with a clear view of filopodia.

In FIG. 13$a$ is a laser scanning confocal microscopic images of mouse fibroblast cells. Cells were cultured for 48 h on horizontally and vertically graphene coated SiO2 and Au substrates, as well as on uncoated controls. For the cultivation, NIH3T3 mouse fibroblast cells were cultured in the complete growth medium (DMEM with High Glucose, 4.0 mM 213 L-Glu, sodium pyruvate and 10% Bovine Calf Serum). Cells were fixed and stained with Live/Dead viability stain. 48 h cultured cells were treated with 20% ethanol for 10 min as a control for cell death.

FIG. 13$b$ shows SEM images of cells grown on vertical graphene coated SiO2 and Au substrate and respective control.

FIG. 13$c$ show High magnification SEM image of a cell on the coated surface, with the clear view of filopodia.

All experiments were performed in three biological replicates and representative images are shown.

These mammalian cells are approximately 20 µm in size, an order of magnitude larger than the bacterial cells (1-2 µm). Presumably, either the size, or the protective matrix secreted by the fibroblasts, made the NIH3T3 resistant to the effects of vertical graphene. This is proven by the SEM images (FIG. 13$b$), where no mechanical damage was visible. In addition to not harming the NIH3T3 cells, vertical graphene seemed to enhance their formation of filopodia (FIG. 13$c$), the actin-based filaments that are involved in cell attachment, sensing the environment, and migration. These results were in line with previous observations that graphene and graphene derivatives enhance the adherence, differentiation and proliferation of mammalian cells, and the here used special vertical coating did not alter this beneficial interaction in any way.

Thus, it was concluded that coated surfaces having the above-discussed coating with standing flakes had no observable effect on fibroblast viability, and does not harm eukaryotic cells.

The SEM imaging discussed above was used to visualize the morphological changes of bacterial cells in the bacterial biofilm. For SEM imaging, the biofilms were rinsed twice with sterile water and fixed with 3% of glutaraldehyde for 2 h. The fixed biofilm samples were dehydrated using graded ethanol (30, 40, 50, 60, 70, 80, and 90 v/v %) each for 10 min and with 100 v/v % for 20 min. The dehydrated samples were kept at room temperature for 2 h to dry completely. Prior to SEM imaging, the samples were coated with a thin layer of gold (5 nm). NIH3T3 cells were fixed with 4% paraformaldehyde for 30 min. Fixed samples were dehydrated using graded ethanol (50 and 70% for 5 min, 80, 95 and 100% for 10 min) and dried on room temperature overnight. Prior to SEM imaging, the samples were coated with a thin layer of titanium (5 nm). SEM imaging was performed with Supra 60 VP (Carl Zeiss AG). Three biological replicates were analyzed for each sample, with five images analyzed per replicate.

The experimental results demonstrate that by controlling the orientation of graphene coatings, it is possible to achieve two very distinct outcomes: bactericidal and neutral. The continuous horizontal CVD monolayer graphene coating consistently had no deleterious effects on attachment or survival of either bacterial or mammalian cells. By contrast vertically aligned graphene coating, i.e. a coating having standing Angstrom scale flakes, was harmless to mammalian cells, but it effectively prevented attachment of bacteria to the coated surfaces, and had a pronounced killing effect on bacterial cells.

These two arrangements of graphene had diametrically opposite effects on bacteria. The horizontal monolayer graphene did not harm either the bacterial cells or mouse fibroblasts, suggesting low risk of cytotoxicity. Vertically grown graphene, on the other hand, caused extensive structural damage to bacterial cells and effectively prevented biofilm attachment to the coated surfaces. However, it did not induce any significant damage to mouse fibroblasts. It is therefore concluded that vertically deposited graphene in the form of standing flakes might therefore be effectively used in prevention of bacterial infections and biofouling, and without negatively effecting eukaryotic cells.

The penetration of graphene into the bacterial cells seems to depend on the angle of contact between the membrane and the exposed edges of the graphene flakes, making the standing flakes very efficient. In the experimental setup the large majority of graphene flakes point away from the substrate plane, as seen e.g. in FIGS. 2a and 2b. By consequence, a high loss of viability was observed.

Even though the above-related experiments are all directed to graphene flakes, it is expected that similar results will be achieved also by somewhat thicker graphite flakes, and also by flakes made of other 2D materials.

The method used for producing vertically coated surfaces provides a uniform array of vertically aligned Angstrom scale flakes. However, many other methods can be used for providing the coating, such as by use of spray coating, lamination, and the like. Depending on the application, and in particular as long as a predominantly vertical alignment of the flakes can be achieved on the surface, sufficient antibacterial effects can seemingly be attained even with simpler coating methods. Further, an antibacterial surface may also be formed on the substrate in other ways than by coating.

CONCLUSION AND SUMMARY

The invention has now been discussed in relation to different embodiments. However, it should be appreciated by those versed in the art that several further alternatives are possible. For example, the antibacterial coating/surface may be used in many other medical devices, as well as in other applications. For example, the coating/surface may be used in other types of catheters, such as vascular catheters or the like, in other type or irrigation systems, in tubes containing bacteria sensitive contents, etc.

Many different materials could also be used for the substrate. Specifically, other polymers or blends of polymers may be used, and additives, such as fillers, compatibilizers, stabilizers, antioxidants, plasticizers, etc may be included. The coating may also have other antibacterial additives, such as silver or the like.

It will be appreciated by those versed in the art that several such alternatives similar to those described above could be used without departing from the spirit of the invention, and all such modifications should be regarded as a part of the present invention, as defined in the appended claims.

The invention claimed is:

1. An antibacterial device comprising a substrate and an antibacterial coating or antibacterial surface provided on at least part of a substrate surface of the substrate, wherein said antibacterial coating or surface comprises Angstrom scale flakes, wherein the Angstrom scale flakes comprise graphene or graphite flakes, the Angstrom scale flakes arranged in a standing position on said substrate surface, and attached to the substrate surface via edge sides thereof, wherein the Angstrom scale flakes form an even piece of material with one dimension, corresponding to thickness thereof, substantially smaller than length and height dimensions thereof, wherein the thickness is in a range of 0.1-10 nm and the height with which the Angstrom scale flakes extend from the antibacterial coating or surface is in a range of 1-500 nm, and wherein the Angstrom scale flakes are arranged in a dense array, with a distance between any adjacent Angstrom scale flakes being less than 10 microns.

2. The antibacterial device of claim 1, wherein the Angstrom scale flakes have a thickness in a range of 1-10 atom layers.

3. The antibacterial device of claim 1, wherein the Angstrom scale flakes have a thickness in a range of 1-5 atom layers.

4. The antibacterial device of claim 1, wherein a distance between any adjacent Angstrom scale flakes is less than 5 µm.

5. The antibacterial device of claim 1, wherein a thickness of at least some of the Angstrom scale flakes tapers towards a free end thereof, opposite to the edge side that is attached to the substrate surface.

6. The antibacterial device of claim 1, wherein a width of at least some of the Angstrom scale flakes tapers towards a free end thereof, opposite the edge side that is attached to the substrate surface.

7. The antibacterial device of claim 1, wherein the device is a medical device.

8. The antibacterial device of claim 7, wherein the device is a urinary catheter.

9. The antibacterial device of claim 1, wherein the device forms an internal lumen, and wherein said antibacterial coating or surface is arranged on an internal surface of the substrate facing said lumen.

10. The antibacterial device of claim 1, wherein the device forms an internal lumen, and wherein said antibacterial coating or surface is arranged on an external surface of the substrate facing away from said lumen.

11. The antibacterial device of claim 1, wherein the device is, or forms part of, a cell growing or cell culture equipment.

12. The antibacterial device of claim 1, wherein the substrate includes a plastic material.

13. The antibacterial device of claim 1, wherein the substrate includes at least one polymer.

* * * * *